US00PP08987P

United States Patent [19]

VandenBerg

[11] Patent Number: Plant 8,987

[45] Date of Patent: Nov. 22, 1994

[54] CHRYSANTHEMUM PLANT NAMED JENNIFER

[75] Inventor: Cornelis P. VandenBerg, Salinas, Calif.

[73] Assignee: Yoder Brothers, Inc., Barberton, Ohio

[21] Appl. No.: 155,240

[22] Filed: Nov. 22, 1993

[51] Int. Cl.[5] ..... A01H 5/00

[52] U.S. Cl. ..... Plt./79

[58] Field of Search ..... Plt. 76, 79

*Primary Examiner*—Howard J. Locker

*Attorney, Agent, or Firm*—Foley & Lardner

[57] ABSTRACT

A Chrysanthemum plant named Jennifer particularly characterized by its flat capitulum form; decorative capitulum type; bronze ray floret color with darker center of the flower; diameter across face of capitulum of 64 to 73 mm when fully opened; spreading branching pattern, with 8 to 9 breaks after pinch when grown outside under natural daylength in fall flowerings and 6 to 7 breaks when grown in 10 cm pots for spring flowerings; natural season flower date of August 23 to 31 when planting rooted cuttings on June 18 to 23 in Salinas, Calif., and September 17 to October 6 when planting rooted cuttings June 15 to June 18 in Hightstown, N.J.; flowering response of 47 to 51 days after rooting in no light/no shade programs in spring in Salinas; plant height of 28 to 38 cm when grown in fall under natural daylength with no growth regulators in New Jersey, and 15 to 18 cm when grown in 10 cm pots in spring with no growth regulator applications; and recommended as mid-season variety.

3 Drawing Sheets

The present invention comprises a new and distinct cultivar of Chrysanthemum, botanically known as *Dendranthema grandiflora*, and referred to by the cultivar name Jennifer.

Jennifer, identified as 8257 (89-744001), was originated from a cross made by Cornelis P. VandenBerg in a controlled breeding program in Salinas, Calif., in March 1988.

The female parent of Jennifer was the cultivar identified as Triumph, a yellow-orange decorative garden mum disclosed in U.S. Plant Pat. No. 5,995.

The male parent of Jennifer was an unnamed seedling identified as 8431 (86-479004) and described as a two-tone bronze-gold decorative garden mum with many disc florets. The male parent was discarded from all programs in October 1988.

Jennifer was discovered and selected as one flowering plant within the progeny of the stated cross by Cornelis P. VandenBerg in September 1989, in a controlled environment in Salinas, Calif.

The first act of asexual reproduction of Jennifer was accomplished when vegetative cuttings were taken from the initial selection in November 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Jennifer are firmly fixed and are retained through successive generations of asexual reproduction.

Jennifer has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Jennifer, which, in combination, distinguish this Chrysanthemum as a new and distinct cultivar:

1. Flat capitulum form.
2. Decorative capitulum type.
3. Bronze ray floret color with darker center of the flower.
4. Diameter across face of capitulum of 64 to 73 mm when fully opened.
5. Branching pattern is spreading, with 8 to 9 breaks after pinch when grown outside under natural daylength in fall flowerings, and 6 to 7 breaks when grown in 10 cm pots for spring flowerings.
6. Natural season flower date of August 23 to 31 when planting rooted cuttings on June 18 to 23 in Salinas, Calif., and September 17 to October 6 when planting rooted cuttings June 15 to June 18 in Hightstown, N.J.
7. Flowering response of 47 to 51 days after rooting in no light/no shade programs in spring in Salinas.
8. Plant height of 28 to 38 cm when grown in fall under natural daylength with no growth regulators in New Jersey, and 15 to 18 cm when grown in 10 cm pots in spring with no growth regulator applications.
9. Recommended as mid-season variety.

The accompanying photographic drawings show typical inflorescence and leaf characteristics of Jennifer, with the colors being as nearly true as possible with illustrations of this type.

Sheet 1 is a color photograph of Jennifer grown outside in Salinas, Calif. and dug and transplanted into 15 cm bulb pans at flowering time for photography purposes.

Sheet 2 is a black and white photograph of three views of the inflorescence of Jennifer.

Sheet 3 is a black and white photograph showing the upper and under sides of the leaves of Jennifer at 3 stages of development (mature, intermediate and immature). In sheets 2 and 3 a measuring tape in centimeters has been added.

Of the commercial cultivars known to the inventor, the most similar in comparison to Jennifer is the cultivar identified as Dark Triumph, disclosed in U.S. Plant Pat. No. 7,905. Reference is made to attached Chart A, which compares certain characteristics of Jennifer to the same characteristics of Dark Triumph.

Similar traits are capitulum form and type, diameter across face of capitulum and plant height in spring flowerings. Jennifer has a darker bronze ray floret color than Dark Triumph. In addition, when compared with Dark Triumph, Jennifer has a later natural season flower date in both Salinas and Hightstown, a slower controlled flowering response in spring, and taller plant height in the fall.

In the following description, color references are made to The Royal Horticultural Society Colour Chart. The color values were determined on plan material grown as a pinched garden mum grown outdoors in Salinas, Calif. on Aug. 23, 1993.

Classification:

*Botanical.*—*Dendranthema grandiflora* cv Jennifer.

*Commercial.*—Flat decorative spray pot mum and garden mum.

INFLORESCENCE

A. Capitulum:

*Form.*—Flat.

*Type.*—Decorative.

*Diameter across face.*—64 to 73 mm when fully opened.

B. Corolla of ray florets:

*Color (general tonality from a distance of three meters).*—Bronze, with darker center of the flower.

*Color (upper surface).*—179B to 179C.

*Color (under surface).*—181A to 181B.

*Shape.*—Cross section of inner ray florets concave, longitudinal section of outer ray florets convex. Petal tips rounded.

C. Corolla of disc florets: No disc florets present.

D. Reproductive organs:

*Androecium.*—Absent; no disc florets present.

*Gynoecium.*—Present on ray florets.

PLANT

A. General appearance:

*Height.*—28 to 38 cm when grown in fall under natural daylength in New Jersey with no growth regulators, and 15 to 18 cm when grown in 10 cm pots in spring in Salinas with no growth regulator applications.

*Branching pattern.*—Spreading, with 8 to 9 breaks after pinch when grown outside under natural daylength in fall flowers, and 6 to 7 breaks when grown in 10 cm pots for spring flowerings.

B. Foliage:

*Color (upper surface).*—147A.

*Color (under surface).*—147B.

*Shape.*—See photograph.

Chart A

COMPARISONS MADE OF PLANTS GROWN UNDER NATURAL SEASON OUTDOOR CONDITIONS IN SALINAS, CALIFORNIA AND IN HIGHTSTOWN, NEW JERSEY AND IN SPRING FLOWERING PROGRAMS IN SALINAS, CALIFORNIA

| | JENNIFER | DARK TRIUMPH |
|---|---|---|
| Ray floret color | Bronze with darker center | Yellow-orange with darker center |
| Capitulum form and type | Flat decorative | Flat decorative |
| Diameter across face of capitulum | 64 to 73 mm | 64 to 70 mm |
| Nat. season flower date: | | |
| in Salinas, CA | Aug 23 to 31 | Aug 16 to 23 |
| in Hightstown, NJ | Sep 17 to Oct 6 | Sep 19 to Oct 4 |
| Controlled response | 47 to 51 days | 41 to 46 days |
| Plant height: | | |
| in natural season fall | 28 to 38 cm | 23 to 30 cm |
| in 10 cm pots spring | 15 to 20 cm | 15 to 20 cm |

I claim:

1. A new and distinct Chrysanthemum plant named Jennifer, as described and illustrated.

* * * * *

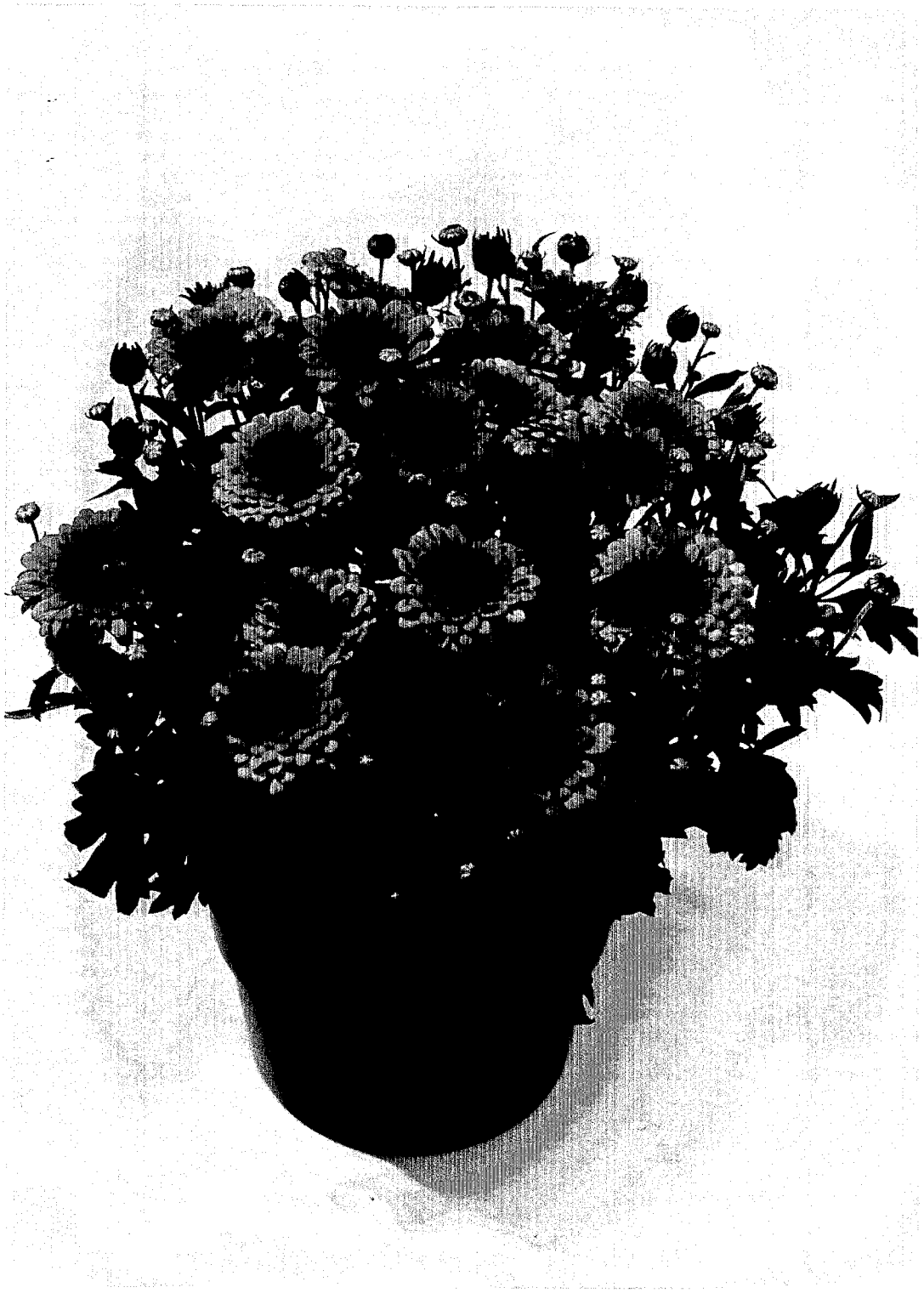

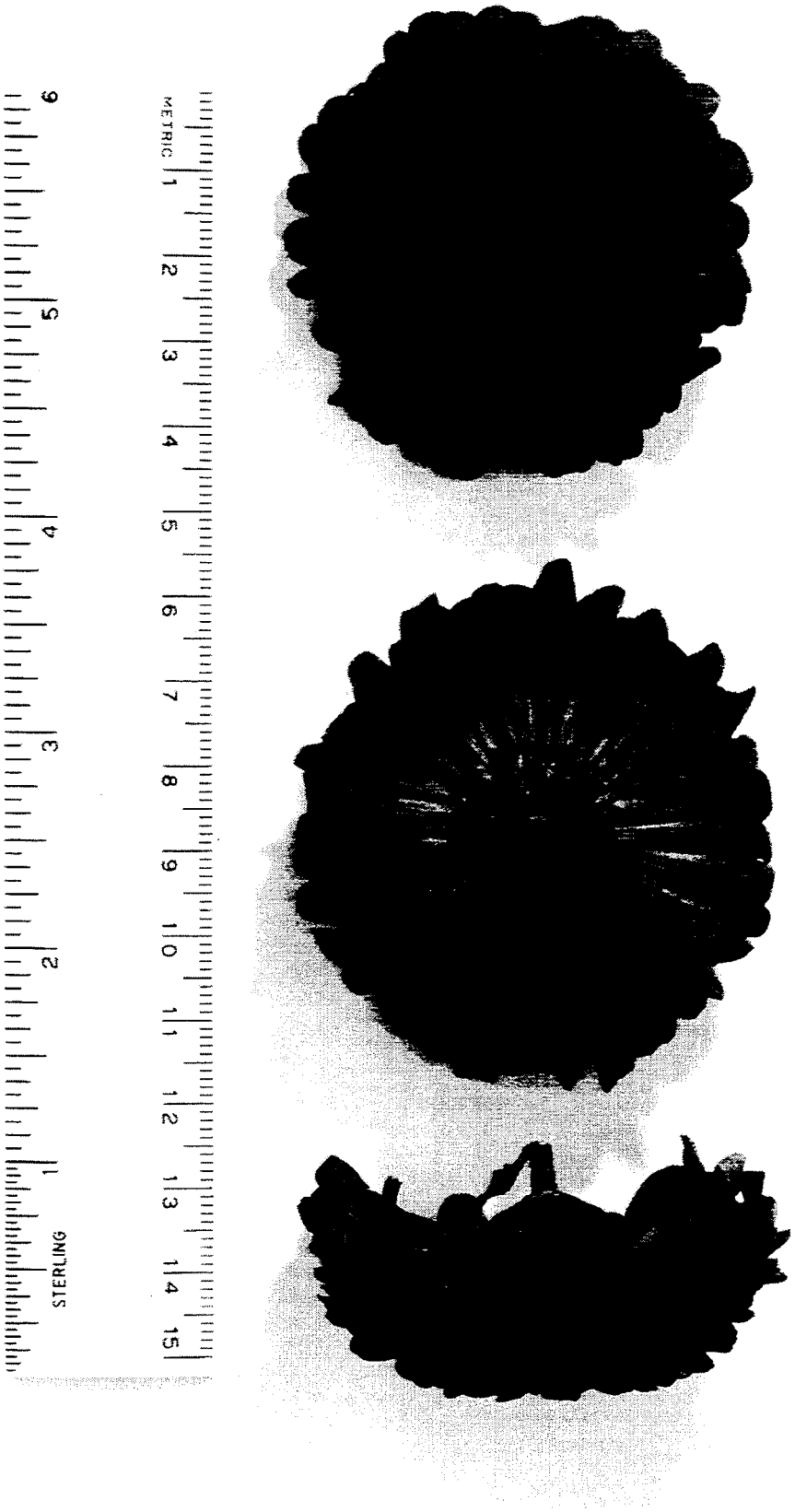
STERLING
METRIC

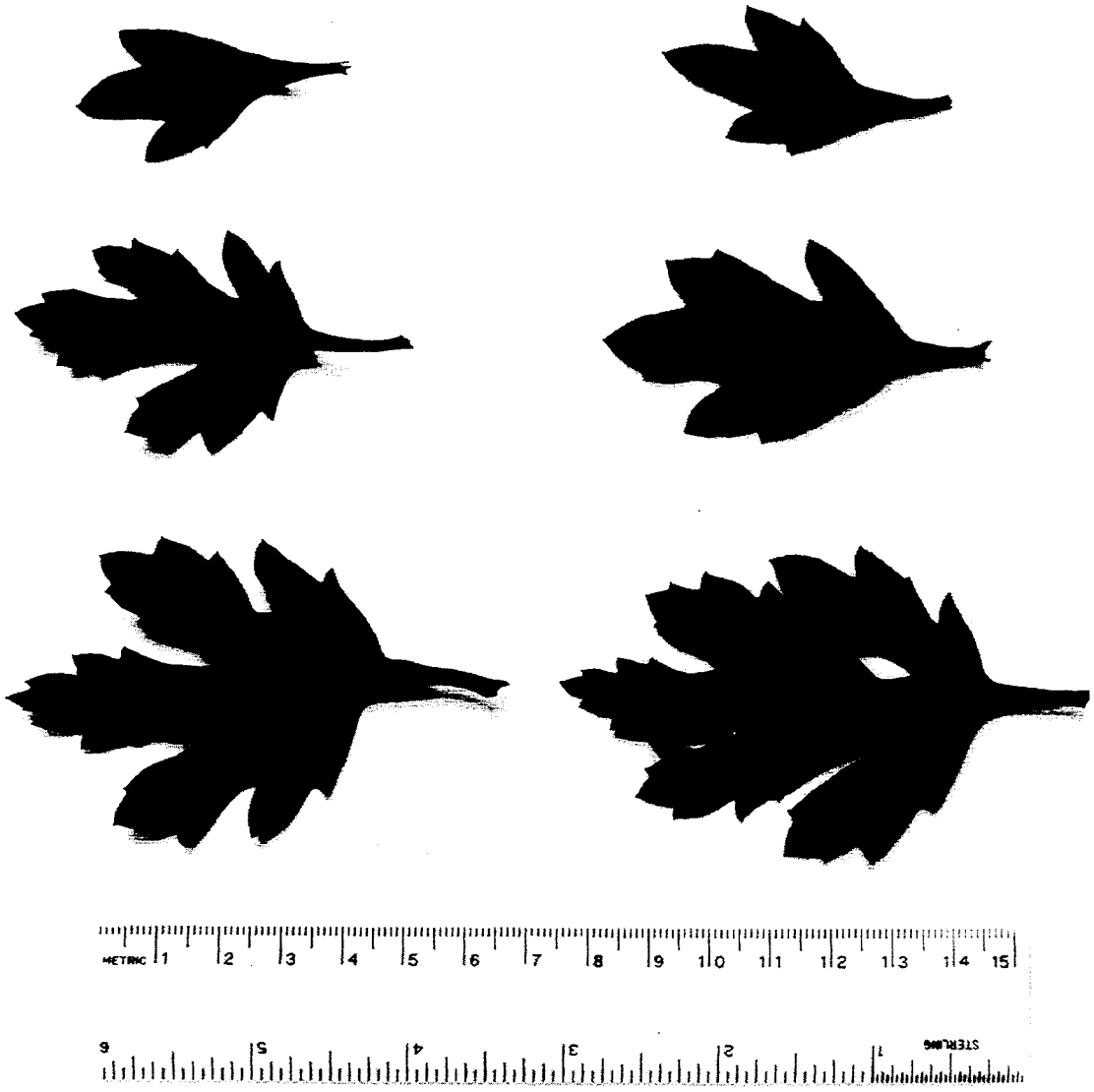
METRIC 1 2 3 4 5 6 7 8 9 10 11 12 13 14 15
STERLING 1 2 3 4 5 6